United States Patent
Cheng et al.

(10) Patent No.: US 12,243,736 B2
(45) Date of Patent: Mar. 4, 2025

(54) PARTICLE MASS SPECTROMETRY

(71) Applicant: Shanghai Polaris Biology Co., Ltd., Shanghai (CN)

(72) Inventors: Yupeng Cheng, Shanghai (CN); Shuangwu Sun, Shanghai (CN)

(73) Assignee: SHANGHAI POLARIS BIOLOGY CO., LTD., Shanghai (CN)

(*) Notice: Subject to any disclaimer, the term of this patent is extended or adjusted under 35 U.S.C. 154(b) by 410 days.

(21) Appl. No.: 17/811,816

(22) Filed: Jul. 11, 2022

(65) Prior Publication Data

US 2023/0005732 A1    Jan. 5, 2023

Related U.S. Application Data

(63) Continuation of application No. PCT/CN2020/072207, filed on Jan. 15, 2020.

(51) Int. Cl.
*H01J 49/40* (2006.01)
*H01J 49/00* (2006.01)
(Continued)

(52) U.S. Cl.
CPC .......... *H01J 49/40* (2013.01); *H01J 49/0031* (2013.01); *H01J 49/025* (2013.01); *H01J 49/0495* (2013.01); *H01J 49/105* (2013.01)

(58) Field of Classification Search
CPC ...... H01J 49/40; H01J 49/0031; H01J 49/025; H01J 49/0495; H01J 49/105
See application file for complete search history.

(56) References Cited

U.S. PATENT DOCUMENTS 6,285,027 B1    9/2001    Chernushevich et al.
8,679,858 B2    3/2014    Nolan et al.
(Continued)

FOREIGN PATENT DOCUMENTS

CN    1689134 A    10/2005
CN    2874764 Y    2/2007
(Continued)

OTHER PUBLICATIONS

Bandura et al., Mass cytometry: technique for real time single cell multitarget immunoassay based on inductively coupled plasma time-of-flight mass spectrometry. Analytical Chemistry 81:6813-6822 (2009).
(Continued)

*Primary Examiner* — Nicole M Ippolito
(74) *Attorney, Agent, or Firm* — WILSON SONSINI GOODRICH & ROSATI

(57) ABSTRACT

Systems and methods are provided for the analysis of single particles with inductively coupled plasma-time of flight mass spectrometry. An ion compression device is operated in combination with an image current detector to improve a duty cycle of particle analysis. The image current detection device is used to determine a start time and an end time of a separate ion cloud which is derived from a single particle. The ion compression device stores and compresses each ion cloud based on instructions from the image current detector. The duty cycle of the particle analysis can be improved up to nearly 100%. The ion compression device is additionally operated with an ion filtration device to achieve a lower detection limit and a higher signal-to-noise ratio.

20 Claims, 9 Drawing Sheets

(51) Int. Cl.
*H01J 49/02* (2006.01)
*H01J 49/04* (2006.01)
*H01J 49/10* (2006.01)

(56) References Cited

U.S. PATENT DOCUMENTS

| | | | |
|---|---|---|---|
| 2002/0175292 | A1 | 11/2002 | Whitehouse et al. |
| 2005/0017166 | A1 | 1/2005 | Scheidemann et al. |
| 2005/0218319 | A1 | 10/2005 | Bandura et al. |
| 2008/0156980 | A1* | 7/2008 | Rather .............. H01J 49/062 250/282 |
| 2013/0037711 | A1* | 2/2013 | Koster ................ G05B 9/03 250/288 |
| 2017/0263427 | A1* | 9/2017 | Benner ............. H01J 49/066 |
| 2019/0295831 | A1* | 9/2019 | Holden ............. H01J 49/022 |
| 2021/0272790 | A1* | 9/2021 | Stewart ............. H01J 49/40 |

FOREIGN PATENT DOCUMENTS

| | | |
|---|---|---|
| CN | 101915800 A | 12/2010 |
| CN | 102939638 A | 2/2013 |
| CN | 103069539 A | 4/2013 |
| CN | 103871820 A | 6/2014 |
| CN | 103972021 A | 8/2014 |
| CN | 104067371 A | 9/2014 |
| CN | 110277299 A | 9/2019 |
| JP | H08166371 A | 6/1996 |
| WO | WO-2015122920 A1 | 8/2015 |
| WO | WO-2017013832 A1 | 1/2017 |

OTHER PUBLICATIONS

Bjornson et al., Single-cell mass cytometry for analysis of immune system functional states. Curr. Opin. Immunol. Aug. 2013;25(4):484-94. doi: 10.1016/j.coi.2013.07.004.

Campbell et al., A new linear ion trap time-of-flight system with tandem mass spectrometry capabilities. Rapid Communications in Mass Spectrometry, vol. 12, 1463-1474 (1998).

Hao et al., Simultaneous High Sensitivity Trace-Element and Isotopic Analysis of Gemstones Using Laser Ablation Inductively Coupled Plasma Time-of-Flight Mass Spectrometry. J. of Gemmology, 35:3, 212-223 (2016).

Racke et al., Detection of small bunches of ions using image charges. Scientific Reports 8:9781, DOI:10.1038/s41598-018-28167-6 (2018), 10 pages.

* cited by examiner (a)

(b)

PARTICLE MASS SPECTROMETRY

CROSS-REFERENCE

This application is a continuation application of International Application No. PCT/CN2020/072207, filed Jan. 15, 2020, the content of which application is incorporated herein by reference.

FIELD OF THE INVENTION

The present disclosure relates generally to particle mass spectrometry. More particularly, the present disclosure relates to a mass spectrometer for analyzing single particles, which is capable of improving at least the duty cycle and sensitivity of particle analysis and reducing the burden of data processing device.

BACKGROUND OF THE INVENTION

In the fields of life science and environment monitoring, the analysis of single particles is of great significance. Mass spectrometry has many advantages such as high sensitivity, fast analysis speed, multi-parameter measurement and high specificity. Mass spectrometry-based techniques have been developed, which greatly improves the performance of single particle analysis. For example, mass cytometry combining mass spectrometry and flow cytometry is developed for single cells analysis. Since it can simultaneously detect more than 40 kinds of proteins, DNA and other biomarkers in a single cell in one run, the mass cytometry significantly improves the capability of function identification and phenotyping of single cells.

In a typical procedure of single-cell analysis based on mass spectrometry, the sample is firstly stained with an antibody reagent binding with specific lanthanide metal elements. The staining process is based on the principle of immune reaction. Different antibodies specifically bind to specific antigens (proteins of cells). Finally, the stained single cells were analyzed by inductively coupled plasma-time of flight mass spectrometry (ICP-TOF MS), which is adapted for simultaneous multi-parameter analysis of single cells, to acquire the information of metal elements, and then the information of corresponding proteins in each single cell can be obtained. The duration of an ion cloud or ion packet generated by a single cell is about 300 μs. For most mass analyzers, such as quadrupole mass filter and quadrupole ion trap, the analysis speed is far from meeting the requirements of simultaneous multi-parameter analysis.

Time-of-flight mass analyzer is an ideal single-cell analysis technology. The analysis cycle can be as low as tens of microseconds, so the earliest mass cytometry is developed based on time-of-flight mass analyzer. However, due to the limitation of the working principle of time-of-flight mass analyzer, it suffers from the problem of low duty cycle, which means only a fraction of ions can be utilized by time-of-flight mass analyzer. It also affects the detection limit and quantitative performance, which results in the difficulty of detecting low expression but meaningful proteins of cells.

SUMMARY OF THE INVENTION

A need exists for systems and methods capable of improving a duty cycle of the TOF analyzer. A need also exists for systems and methods for the MS-TOF analyzer having a lower detection limit and a higher signal-to-noise ratio. The ion compression device provided in the disclosure can be operated in combination with an image current detector to improve a duty cycle of the TOF analyzer up to nearly 100%. In addition, the ion compression device provided in the disclosure can be operated together with an ion filtration device to achieve a lower detection limit and a higher signal-to-noise ratio.

Disclosed herein is a mass spectrometer for analysis of single particles. The mass spectrometer can comprises a sample introduction device, an ionization device, a vacuum interface, an ion image current detector, an ion compression device, a time-of flight (TOF) mass analyzer and a data processing device. The sample introduction device can be configured to sequentially generate and transfer the single particles. The ionization device can be configured to generate an individual ion cloud from each of the single particles received from the sample introduction device. The vacuum interface can be configured to transport the ion clouds from the ionization device with aid of a vacuum. The ion image current detector can be configured to receive the ion clouds from the vacuum interface and collect timing information of each of the ion clouds passing through the ion image current detector. The ion compression device can be configured to (1) receive an individual ion cloud from the ion image current detector, (2) axially compress the received ion cloud based on the timing information of the individual ion cloud, and (3) transport the compressed ion cloud. The TOF mass analyzer can be configured to receive the compressed ion clouds from the ion compression device and separate ions having different masses within the compressed ion clouds to arrive at an ion detector at different times. The data processing device can be configured to process an ion flow signal generated from the ion detector and form a mass spectrum for identification of the ion clouds.

Disclosed herein is a method for analyzing single particles via a mass spectrometer. The method can comprise sequentially generating and transferring the single particles at a sample introduction device; generating, with aid of an ionization device, ion clouds from the single particles received from the sample introduction device; transporting, using a vacuum interface, the ion clouds from the ionization device with aid of a vacuum; receiving, via an ion guide device, the ion clouds from the vacuum interface, and transporting the ion clouds; receiving, via an ion image current detector, the ion clouds from the ion guide device, and collecting timing information of the ion clouds passing through the ion image current detector; receiving, at an ion compression device, an individual ion cloud from the ion image current detector, axially compressing the received ion cloud based on the timing information of the individual ion cloud, and transporting the compressed ion cloud; receiving, at a time-of flight (TOF) mass analyzer, the compressed ion clouds and separating ions having different masses within the compressed ion clouds to arrive at an ion detector at different times; and processing, via a data processing device, an ion flow signal from the ion detector and form a mass spectrum for identification of the ion clouds.

The single particles can be tagged with metal isotopes, such that the ion clouds can comprise ion clouds of the metal isotopes. The single particles can be single cells, biological molecules, or polymer microspheres.

The sample introduction device can be configured to sequentially receive and transfer the single particles from a sample storage device. The sample introduction device can be configured to sequentially generate the single particles from an analyzed sample The ionization device can be an inductively coupled plasma (ICP) ionization device. In some instances, the ionization device can be configured to evaporate, atomize, and ionize the single particles. The ionization device can be configured to generate monoatomic or polyatomic ions from the single particles. In an embodiment, the ionization device can be selected from the group comprising inductively coupled plasma ionization device, secondary ion mass spectrometry ionization device, electrospray ionization device, atmospheric pressure chemical ionization device, and atmospheric pressure photoionization device. The ionization device can be positioned at an atmospheric pressure environment.

The vacuum interface can comprise two or more cone shaped components. In an embodiment, the two or more cone shaped components can be perforated. In some instances, the vacuum interface can comprise two or more adjacent vacuum chambers. A corresponding vacuum pump can be provided for each of the vacuum chambers.

In an embodiment, the mass spectrometer can further comprise an ion guide device positioned at a downstream side of the vacuum interface and at an upstream side of the ion image current detector. The ion guide device can be configured to receive the ion clouds from the vacuum interface and transport the ion clouds. The ion guide device can utilize a quadrupole arrangement, a multipole arrangement, an electrostatic lens, an ion tunnel or an ion funnel. The ion guide device can have a straight shape or a curved shape. The ion guide device can be configured to guide ion clouds to travel along a length thereof. In some instances, the ion guide device can be further configured to effect ion manipulations. The ion manipulations can comprise noise removal and ion focusing. In an embodiment, the ion guide device can comprise at least a first electrode and a second electrode. A first voltage can be applied to the first electrode, and a second voltage different from the first voltage can be applied to the second electrode. The ion guide device can be configured to focus ions radially upon application of the first voltage and the second voltage.

The timing information of the individual ion cloud, as collected by the ion image current detector, can comprise a start time and an end time of the individual ion cloud. In an embodiment, the ion image current detector can be configured to determine the start time of an individual ion cloud passing through the ion image current detector if an image current corresponding to the individual ion cloud is higher than a predetermined threshold, and determine the end time of the individual ion cloud passing through the ion image current detector if the image current is lower than the predetermined threshold, said image current being resulted from charges accumulated on a surface of the ion image current detector due to electrostatic attraction by the ion cloud. In some instances, the ion image current detector can comprise one or more cylinder electrodes.

The ion compression device can be selected from a group comprising a three-dimensional (3D) ion trap, a linear ion trap, an ion funnel, an ion tunnel, an ion carpet, a segmented quadrupole and a segmented multipole. In an embodiment, the ion compression device can comprise a front endcap, a rear endcap, and a ring electrode positioned therebetween. The front endcap and the rear endcap can each be a perforated cone-shaped component with vertexes thereof being adjacent to each other. The ring electrode comprises a convex inner surface.

The ion guide device, the ion image current detector, the ion compression device and the TOF mass analyzer can each be positioned in a vacuum chamber. In an embodiment, the ion image current detector and the ion compression device can be positioned in one vacuum chamber. A corresponding vacuum pump can be provided for each of the vacuum chambers.

In an embodiment, the mass spectrometer can further comprise an ion filtration device positioned at a downstream side of the ion guide device and at an upstream side of the ion image current detector. The ion filtration device can be configured to remove inference ions from the ion clouds. The ion filtration device can comprise a quadrupole arrangement or a multipole arrangement. In some instances, at least two of the ion filtration device, the ion image current detector and the ion compression device can be positioned in one vacuum chamber.

In another embodiment, the mass spectrometer can further comprise an ion filtration device positioned at a downstream side of the ion image current detector and at an upstream side of the ion compression device. The ion filtration device can be configured to remove inference ions from the ion clouds. In some instances, at least two of the ion filtration device, the ion image current detector and the ion compression device can be positioned in one vacuum chamber.

Further disclosed herein is a device for compressing ion groups for use in a mass spectrometer. The device can comprise an ion image current detector configured to receive ion clouds and determine a start time and an end time of each of the ion clouds passing through the ion image current detector; and an ion compression device configured to (1) receive an individual ion cloud from the ion image current detector, (2) axially compress the received ion cloud based upon the start time and the end time of the individual ion cloud, and (3) transport the compressed ion cloud.

Further disclosed herein is a method of compressing ion groups via a device for compressing ion groups for use in a mass spectrometer. The method can comprise receiving, at an ion image current detector, ion clouds and determining a start time and an end time of each of the ion clouds passing through the ion image current detector; and receiving, at an ion compression device, an individual ion cloud from the ion image current detector, axially compressing the received ion cloud based upon the start time and the end time of the individual ion cloud, and transporting the compressed ion cloud.

In an embodiment, the ion compression device can comprises: a front endcap provided at a first end of the ion compression device; a rear endcap provided at a second end of the ion compression device, said second end being opposite to the first end in an axial direction of the ion compression device; and a ring electrode positioned between the front endcap and the rear. The front endcap and the rear endcap can each be perforated cone-shaped component with vertexes thereof being adjacent to each other endcap. The ring electrode can comprise a convex inner surface.

The ion image current detector can be configured to determine the start time of the individual ion cloud passing through the ion image current detector if an image current corresponding to the individual ion cloud is higher than a predetermined threshold, and determine the end time of the individual ion cloud passing through the ion image current detector if the image current is lower than the predetermined threshold, said image current being resulted from charges accumulated on a surface of the ion image current detector due to electrostatic attraction by the ion cloud. In an embodiment, the ion image current detector can comprise one or more cylinder electrodes. The ion image current detector and the ion compression device can be positioned in a vacuum chamber. A vacuum pump can be provided for the vacuum chamber.

Additional aspects and advantages of the present disclosure will become readily apparent to those skilled in this art from the following detailed description, wherein only exemplary embodiments of the present disclosure are shown and described, simply by way of illustration of the best mode contemplated for carrying out the present disclosure. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
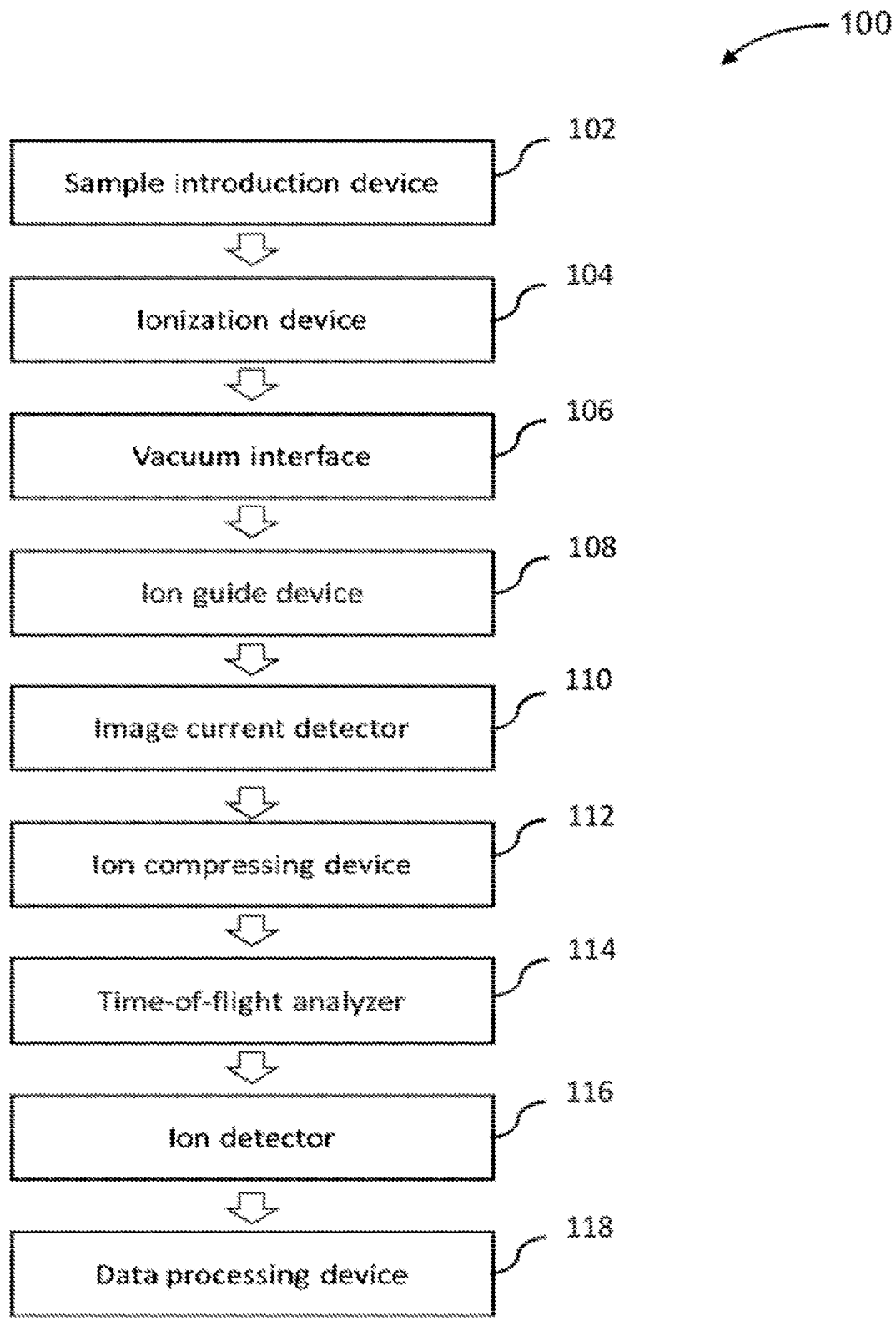
FIG. 1 shows a block diagram of an exemplary mass spectrometer for analysis of single particles in accordance with some embodiments of the disclosure.

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Systems and methods for mass spectrometry are provided. The systems and methods can be capable of analyzing single particles and may at least improve a duty cycle and sensitivity of the particle analysis. A mass spectrometer can comprise a sample introduction device, an ionization device, a vacuum interface, an ion guide device, an image current detector, an ion compression device, a time-of-flight mass analyzer, a detector, and a data processing system. The well-prepared particle sample is transferred to the ionization device through the sample introduction device for ionization to derive an individual ion cloud for each particle. After passing through the vacuum interface, the ion cloud enters the vacuum system of mass spectrometer. Then, the ion cloud is transported by the ion guide device to the downstream image current detector. The image current detector is used to determine a timing information, for example the start and end time, of the ion cloud. When the ion cloud arrives, the image current detector picks up a signal higher than the pre-determined threshold value, and it simultaneously triggers the downstream ion compression device to receive and axially compress the ion cloud. When the image current signal falls down to a level lower than the threshold, the ion compression device stops receiving ions. Then, the compressed ion cloud is pushed to the downstream time-of-flight (TOF) mass analyzer. After mass separation in the time-of-flight mass analyzer, the ions arrive at the detector one after another according to the mass sequence (e.g., from low to high) and a corresponding signal sequence is generated. The signal is then processed by the data processing device to obtain the mass spectrum.

Considering that interference ions can affect the sensitivity of the image current detector and the effective capability and storage of the ion compression device, an ion filter device can be added upstream of the ion compression device. The ion filter device can remove ions with specific mass, such as the interference ions.

Systems and methods provided herein may utilize timing information collected by the image current detector to inform operation of the ion compression device. The ion compression device may be able to apply and adjust its operation mode from a non-compression mode into an ion compression mode in response to whether the system predicts a presence of an ion cloud within the ion compression device based on the timing information. By allowing such responsiveness, the systems and methods may be able to improve a duty cycle of the TOF analyzer up to nearly 100%.

FIG. 1 shows a block diagram 100 of an exemplary mass spectrometer for analysis of single particles in accordance with some embodiments of the disclosure. As shown in FIG. 1, the particle mass spectrometer 100 disclosed in the disclosure can comprise a sample introduction device 102, an ionization device 104, a vacuum interface 106, an image detection device 110, an ion compression device 112, a time-of-flight (TOF) mass analyzer 114, an ion detector 116 and/or a data processing device 118. Any of these components are provided by way of example. These components may be provided in a different order. Any of these components may be removed or replaced. In an embodiment, an ion guide device 108 can be provided at a downstream side of the vacuum interface and at an upstream side of the ion image current detector. In an embodiment, the sample introduction device and the ionization device can be positioned at a substantially atmospheric pressure environment, while the ion guide device, the image detection device, the ion compression device, the time-of-flight mass analyzer and the ion detector can be positioned in a pressure reduced environment or a vacuum environment. The vacuum interface can be the interface between the substantially atmospheric pressure environment and the pressure reduced environment.

The sample introduction device 102 can be configured to sequentially generate and transfer samples from a sample storage device to the ionization device 104. The sample introduction device can be selected from the group consisting of a liquid chromatography, a syringe pump, a pneumatic pump, a peristaltic pump, a microfluidic device, a surface acoustic wave atomization device, a pneumatic spray device, an inkjet atomization device, a laser desorption device or a combination thereof.

The sample introduction device can be configured to change an original state of sample (e.g., a liquid state or a solid state) to a state that meets the requirement of the downstream ionization device. In an embodiment, the sample introduction device can change a state of the sample to a certain ordered distribution or a free dispersion of single particles in a gas phase. For instance, the sample introduction device can generate single particles from the sample. In an embodiment, the sample introduction device can comprise a droplet generator, which is used to generate single particle droplets from the sample and deliver the generated single particle droplets to the ionization device. Single particles can include single cells, beads, polymer microspheres, biological molecules, polymer microspheres, or aerosols. Metal isotope tagged antibodies can be used to bind antigens found on or within a cell. In some instances, over 10, 50, 100, 200 or more antigens can be simultaneously detected in a single cell using unique metal isotope tags on corresponding antibodies. To avoid interference with elements found in the cells, lanthanide elements are preferred as metal isotope tags. Examples of metal isotope tags can include lanthanum, cerium, prasedymium, neodymium, promethium, samarium, europium, gadolinium, terbium, dysprosium, holmium, erbium, thulium, ytterbium, lutetium, or any other isotope.

Single particles can be encapsulated in a carrier. For instance, a single cell can be encapsulated in a carrier. The carrier can form a droplet that partially or completely surrounds the particle. The particle can be suspended within the carrier droplet. The carrier can be a carrier fluid, such as water, mixture of water and oil, and mixture of water and organic solvent. A droplet generator can be used to yield individual sample droplets which may include particles within the carrier fluid droplets.

The ionization device 104 can be configured to generate an individual ion cloud for each single particle received from the sample introduction device. The ions can be monoatomic or polyatomic ions. Depending on the type of ions to be analyzed, the ionization device can be selected from the group consisting of an inductively coupled plasma (ICP) ionization source, a secondary ion mass spectrometry ionization source, an electrospray ionization source, an atmospheric pressure chemical ionization source, or an atmospheric pressure photoionization. In an embodiment, the ionization device can be an ICP ionization device where the single particles tagged with metal isotopes are evaporated, atomized, and ionized to generate ion clouds of metal isotopes. An ion cloud can mean a cluster of ions. In an embodiment of the disclosure, an ion cloud or ion packet can mean an individual group of ions derived from a single particle. A density or a generation frequency of ion cloud can depend on a particle density in a sample solution and a flow rate of a sample introduction device. A density of ion cloud can be more than or equal to 10 cells per second, 50 cells per second, 100 cells per second, 500 cells per second, 1000 cells per second, 1500 cells per second, or 2000 cells per second. A size of an ion cloud can be 0.1 millimeter (mm), 0.5 mm, 1 mm, 5 mm, 10 mm, 15 mm, 20 mm, 40 mm, 60 mm, 80 mm or 100 mm. A duration time of an ion cloud can be 1 microsecond (µs), 40 µs, 80 µs, 100 µs, 200 µs, 400 µs, 600 µs, 800 µs, 1000 µs, 2000 µs, 4000 µs or 5000 µs.

The vacuum interface 106 can be configured to transport the ion clouds from the ionization device with aid of a vacuum. The vacuum interface is provided to isolate an atmospheric environment from a vacuum system, and simultaneously serves as an inlet of ions entering the vacuum. The vacuum interface can comprise dual cones, triple cones or capillary columns. In an embodiment, the vacuum interface can comprise two or more cone shaped components which are perforated. The vacuum interface can comprise two or more adjacent vacuum chambers where a corresponding vacuum pump is provided for each of the vacuum chambers.

The ion image current detector 110 can be configured to receive the ion clouds from the vacuum interface and determine a timing information, for example a start time and an end time, of each of the ion clouds passing through the ion image current detector. The determination of timing information of each ion cloud is effected by detecting an image current generated from image charges accumulated on the ion image current detector due to an electrostatic attraction effect when the ion cloud approaches the image current detector.

In an embodiment, the ion guide arrangement 108 can be further provided at a downstream side of the vacuum interface and at an upstream side of the ion image current detector. The ion guide arrangement can be configured to receive the ion clouds from the vacuum interface and transport the ion clouds to downstream devices. The ion guide arrange can be configured to effect ion manipulations to refine the ions. Examples of ion manipulations can include ion noise removal and ion beam focusing. The ion guide arrangement can be selected from the group consisting of quadrupole, hexapole, octupole, ion funnel, ion tunnel, electrostatic lens or a variation or combination thereof.

The ion compression device 112 can be configured to receive an individual ion cloud from the ion image current detector based upon the start time and the end time of the individual ion cloud as determined by the ion image current detector, axially compress the received ion cloud, and transport the compressed ion cloud to a downstream device. The ion cloud can be stored and compressed individually within the ion compression device, such that a time duration of the ion cloud for each particle can be narrowed down significantly. Thus, the ion cloud of each particle can be transported to the time-of-flight mass analyzer 114.

The time-of flight mass analyzer 114 can be configured to receive the compressed ion clouds from the ion compression device and separate ions having different masses within the compressed ion clouds to arrive at the ion detector 116 at different times. As the ion cloud is axially compressed to have a narrow duration, the ions within the ion cloud can be analyzed by the time-of-flight mass analyzer in one shot instead of multiple shots. When ions arrive at the ion detector 116 in a mass order (e.g., from low to high), a corresponding signal sequence can be generated, which is processed by the data processing device 118 to obtain a mass spectrum of the particle.

Figure 2:
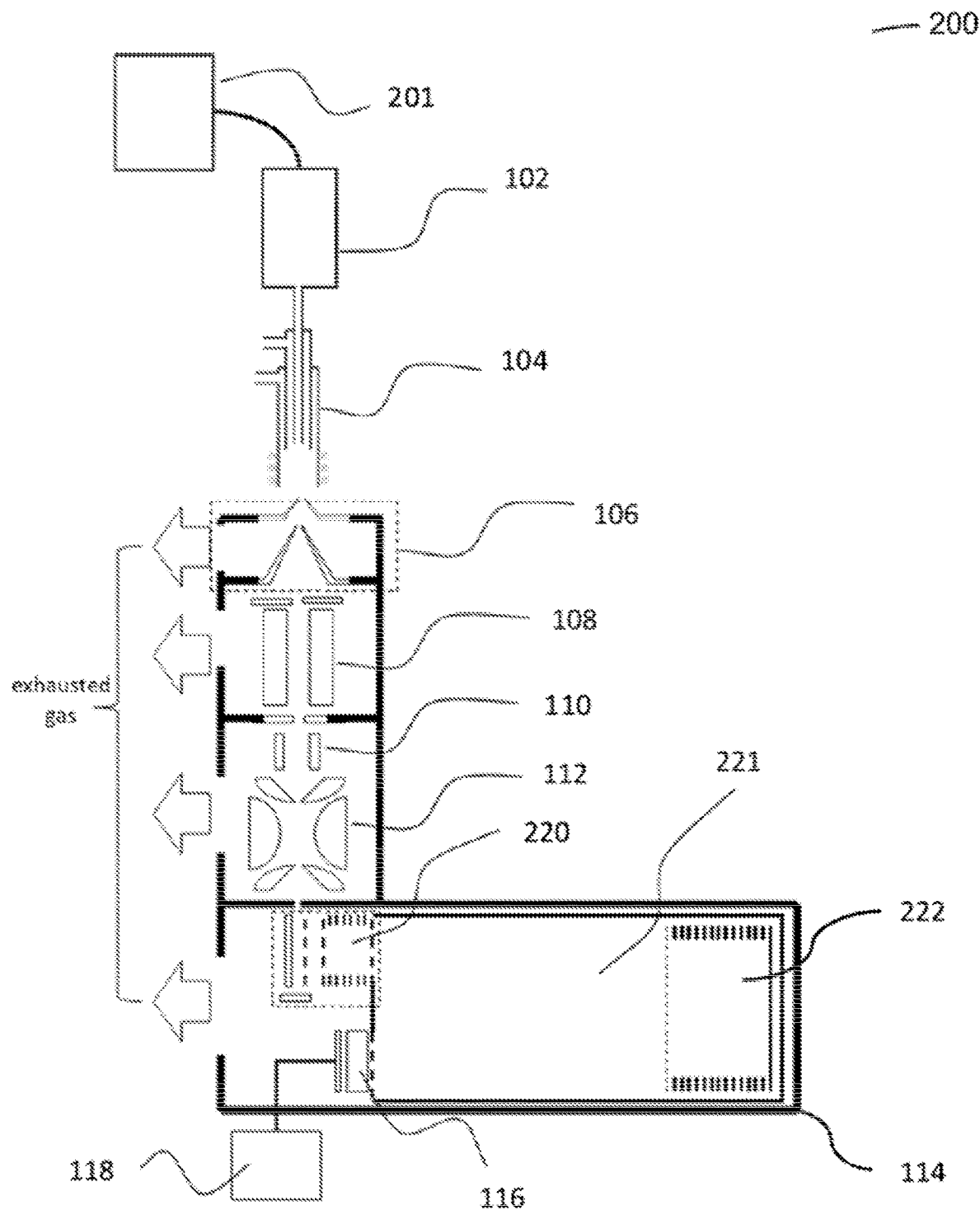
FIG. 2 shows an exemplary structure of a particle mass spectrometry for analysis of single particles in accordance with some embodiments of the disclosure.

FIG. 2 shows an exemplary structure of a particle mass spectrometry 200 for analysis of single particles disclosed in accordance with some embodiments of the disclosure. Samples can be transferred from a sample storage device 201 to the sample introduction device 102 where single particles can be generated and tagged with metal isotopes in order to generate a sequence of single particles in a gas phase. The tagged particles can be transported from the sample introduction device 102 to the ionization device 104.

The ionization device 104 can be an inductively coupled plasma (ICP) ionization device. Within the ICP ionization device, metal isotopes used to tag each of the single particle can be evaporated, atomized and ionized to generate a corresponding ion cloud. The ion cloud can be a metal isotopes cloud. Alternatively, the ICP ionization device can be replaced by a microwave plasma torch (MPT), glow discharge ionization (GDI), or laser ionization (LI) among others.

The ion cloud is then placed into a vacuum system of mass spectrometer through the vacuum interface 106. The vacuum interface can be the interface between a substantially atmospheric pressure environment and a pressure-reduced environment. The vacuum interface can comprise two or more cone-shaped components which are perforated. The two or more cone-shaped components can separate two or more adjacent vacuum chambers. A hole size of the perforated cone-shaped component can limit a volume of gas that passes through each component. A corresponding vacuum pump can be provided for each vacuum chamber allowing a gas pressure to gradually decrease from upstream to downstream. The pressure drop gradient can be greatest near the boundary of the two chambers. This pressure drop can cause a supersonic expansion. The shape, hole size, inter distance and voltages applied to the vacuum chamber can be optimized depending on the application.

Then, the ion clouds can be transported to image current detector 110. In an embodiment, the ions can be directed to pass through the ion guide device 108 prior to being transported to image current detector 110. The ion guide device can receive the metal isotope ion clouds from the upstream perforated cone-shaped components and guide the ion clouds to travel along a length of the ion guide device. The ion guide device can comprise two or more electrodes. The electrodes can be generally parallel to each other. Each electrode can comprise one or more working surfaces. The working surfaces of the electrodes can face one another. A gap can be provided between the working surfaces. The region between the working surfaces may be an ion channel. Upon proper application of voltages to the electrodes, the electrodes can generate an electric field that manipulates the ions travelling along the gap.

The ion guide device can be chosen from an electrostatic lens, a quadrupole, a multipole, an ion tunnel, an ion funnel, or a combination thereof. In an embodiment, the ion guide device can be configured to effect ion manipulations. The ion manipulations can be determined according to a variety of practical requirements and include at least one of the following: (1) selectively filtering ions with a specific mass, (2) ion bunching; or (3) ion storage. The purpose of effecting ion manipulations is to improve the performance, including duty cycle, resolution, space charge and so on, of the downstream devices.

A linear ion guide device is shown in the example of FIG. 2. However, curved ion guide devices can be employed which can provide several advantages including (1) removing neutral noise from a variety of gas molecules in the environment to increase the signal to noise ratio and decrease the gas burden of the vacuum pump, and (2) increasing the flexibility of the instrument design by decreasing the instrument footprint. The ion guide can be shaped so as to provide a 90 degree turn or a 180 degree turn in the focused ion path. Any degree of curvature may be provided. Degrees of curvature can include less than or equal to 90 degrees, 95 degrees, 100 degrees, 105 degrees, 110 degrees, 115 degrees, 120 degrees, 125 degrees, 130 degrees, 135 degrees, 140 degrees, 145 degrees, 150 degrees, 155 degrees, 160 degrees, 165 degrees, 170 degrees, 175 degrees, or 180 degrees.

The ion clouds can then be transported to the image current detector 110. The image current detector can be configured to determining a timing information, for example a start time and an end time, of each ion cloud passing through the image current detector. In the process of ion cloud approaching, passing through and/or leaving the image current detector, the image current detector can sense a signal which is correlated with the ion cloud and indicative of the approaching, passing through and/or leaving the image current detector. In some instances, the sense signal may occur when an ion cloud is within a predetermined proximity of the image current detector. In some instances, the sensed signal may occur only or primarily when the ion cloud is within the image current detector or immediately adjacent to the image current detector. In some instances, a sensed signal may be triggered when the ion cloud is entering the image current detector or entering within a proximity of the image current detector. Optionally, a sensed signal may be modified or decreased when the ion cloud is exiting the image current detector or exiting a proximity of the image current detector. The sensed signal can be an image current. The image current is generated from image charges which are accumulated on the ion image current detector. The image charges are induced due to an electrostatic attraction effect when the ion cloud approaches, passes through and leaves the image current detector.

Timing information relating to the presence of the ion cloud may be calculated based on the image current. For instance, when the sensed signal is higher than a predetermined threshold, the timing may be triggered to indicate a start time for the presence of the ion cloud. When the sensed signal falls beneath the predetermined threshold, the timing may be triggered to indicate an end time for the presence of the ion cloud. In some embodiments the timing information may be collected and utilized with a high degree of precision and/or accuracy. The timing information may be provided within an order of miliseconds (ms). The timing information can be provided with a degree of precision and/or accuracy more than or equal to 1 ms, 0.5 ms, 0.1 ms, 0.05 ms, 0.01 ms, 0.005 ms, or 0.001 ms. In some embodiments, timing information may include a start time for a presence of the ion cloud and/or end time for a presence of the ion cloud as it passes the image current detector. In some instances, other timing information such as peak time (e.g., when ion cloud is a greatest density) may be collected. In some instances, timing information when the ion cloud reaches one, two, three, or more specified thresholds of density may be collected. In some instances, a length of time may be calculated relating to the ion cloud. For instance, a difference between a start time and end time may be calculated to determine a length of time it takes for an ion cloud to pass.

When the sensed signal is higher than a predetermined threshold value, the downstream ion compression device 112 can be triggered to receive and axially compress the ion cloud. In an embodiment, the ion compression device can switch from a non-compression state into an ion compression state in response to the sensed signal which is higher than the predetermined threshold value. In the non-compression state, the ion compression device may receive ions but apply no compression voltage to the ions. Optionally, in the non-compression state, the ion compression device may not receive ions. In the ion compression state, the ion compression device may apply appropriate compression voltage to the ions. When the sensed signal falls down to a level lower than the threshold, the ion compression device stops receiving ions.

The ion compression device may receive timing information from the image current detector, or may receive instructions from an additional component that may utilize the timing information from the image current detector. The compression device may be immediately adjacent to the image current detector or may be further downstream from the image current detector. In some instances, a distance between the image current detector and the ion compression device may be less than or equal to 10 cm, 5 cm, 3 cm, 2 cm, 1 cm, 5 mm, 3 mm, 1 mm, 0.5 mm, 0.1 mm, 0.05 mm, 0.01 mm or less. In some instances, a distance between the image current detector and the ion compression device may be known. In some instances, an amount of time for an ion cloud to travel from the image current detector to the ion compression device may be known or calculated based on distance and rate of flow, as well as experiment measurements. The timing information may be used in conjunction with known distance and/or travel time from the image current detector to the image compression device to affection operation of the ion compression device.

Operation of the compression device may include varying working conditions, including DC voltages, RF voltages, local gas pressure and a combination thereof, based on the timing information from the image compression device. The ion cloud may be compressed by confinement of DC potential barrier, RF pseudopotential well, and/or gas collisional cooling. The combination of utilizing the timing information in varying the working conditions may allow improvement of duty cycle and signal to noise ratio of particle analysis by targeted compression of ion cloud.

After compression in the ion compression device, the compressed ion cloud, as a whole, can be pushed into an orthogonal accelerator 220 of the TOF mass analyzer 114. After the compressed ion cloud is accelerated to a specific kinetic energy by the orthogonal accelerator, the accelerated ion cloud can fly into a field-free flight tube 221 for mass separation. A flight path of the ion cloud can be reflected by a reflector 222 which is positioned at an opposite end of the orthogonal accelerator in the TOF mass analyzer. Due to a difference in flight speed of ions having different masses in the ion cloud, the ions can arrive at the detector 116 in a mass order (e.g., from low to high). An ion flow signal can be generated from the detector and further processed by the data processing device 118, such that a mass spectrum of the ion cloud, which is derived from a single particle, can be obtained for qualitative and quantitative identification of a composition of the single particle.

The ion guide device, the image detection device, the ion compression device and the time-of-flight mass analyzer can each be positioned within a vacuum chamber. A corresponding vacuum pump can be provided for each of the vacuum chambers. In an embodiment, the image detection device and the ion compression device can be positioned in a same vacuum chamber. A pressure in a vacuum chamber for the ion guide device can be provided in a range from 0.001 to 1000 Pascal (Pa). In an example, the pressure in the vacuum chamber for the ion guide device can be about 1 Pa. A pressure in a vacuum chamber for the image detection device and the ion compression device can be provided in a range from 0.0001 to 10 Pa. In an example, the pressure in the vacuum chamber for the image detection device and the ion compression device can be about 0.01 Pa. A pressure in a vacuum chamber for the TOF analyzer can be provided in a range from 0.00001 to 0.001 Pa. In an example, a pressure in the vacuum chamber for the TOF analyzer can be about 0.0001 Pa. The vacuum interface can create an isolation between and a transition from the atmospheric environment to the downstream vacuum system. In an example, a pressure in the vacuum interface can be provided in a range from 0.1 to 2000 Pa. In an example, a pressure in the vacuum interface can be about 100 Pa.

Figure 3:
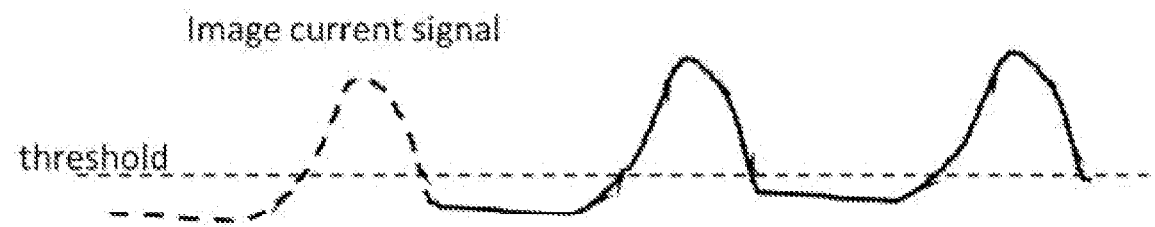
FIG. 3 is a schematic of image detection device based on single cylinder electrode in accordance with some embodiments of the disclosure, panel (a) showing an example of an image current signal, and panel (b) showing an example of image detection device and ion clouds.
Figure 3:
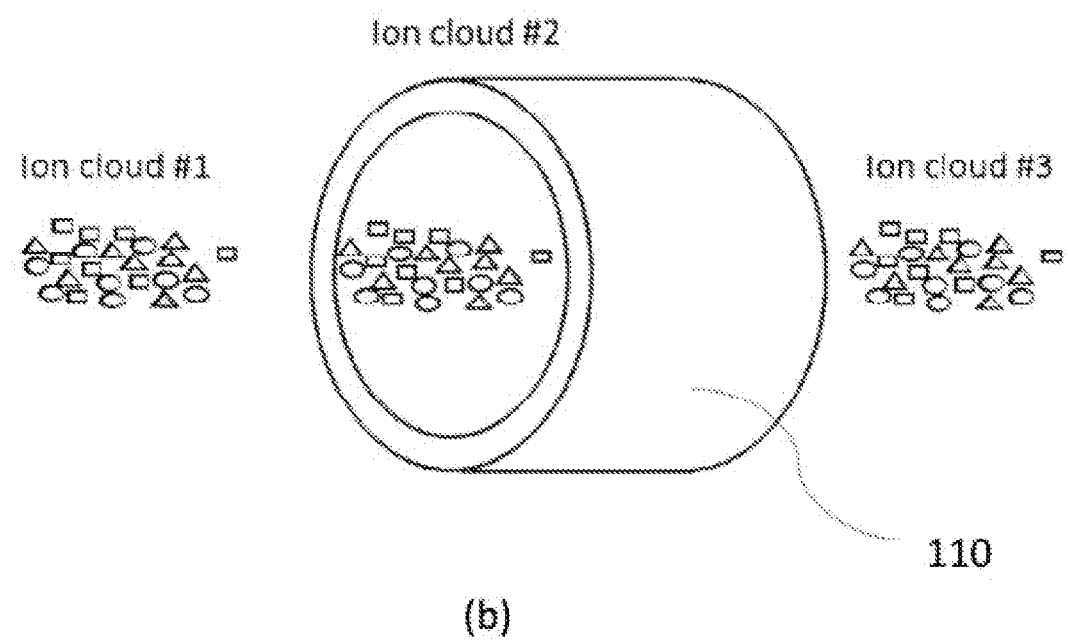

FIG. 3 is a schematic of image current detector based on single cylinder electrode in accordance with some embodiments of the disclosure. Panel (a) of FIG. 3 shows an example of an image current signal, and panel (b) of FIG. 3 shows an example of image detection device and ion clouds. The image current detector 110 can be configured to determine a timing information of a separate ion cloud, for example a time at which a separate ion cloud approaches (e.g., a starting time) and a time at which the separate ion cloud leaves (e.g., an ending time) in a non-destructive manner. The image current detector can comprise a cylinder metal electrode. When moving ions (e.g., ion cloud) get close to a surface of the metal electrode, due to an electrostatic attraction, an amount of charges with opposite polarity will be accumulated on the surface of the electrode, which is called image charge. The number of image charge is increased with an increase in a number of the moving ions and a proximity of the moving ions relative to the electrode surface. As the moving ions approach and leave, the amount of image charge varies over time. Thus, an image current generated from the image charge can be detected from the electrode, as shown in panel (a) of FIG. 3.

In the example shown in panel (b) of FIG. 3, a cylinder electrode can be used as the image current detector. When the ion cloud approaches, passes through and leaves the cylinder electrode, a corresponding image current can be detected from the cylinder electrode. Once the ion cloud approaches and enters an entrance opening of the cylinder electrode, an image current can be higher than a predetermined threshold. At this time, a start signal can be generated to instruct the downstream ion compression device to receive and compress ion cloud. Once the ion cloud totally passes through the cylinder electrode and leaves an exit opening of the cylinder electrode, the image current can be lower than the threshold. At this time, a stop signal can be generated to instruct the ion compression device to stop receiving the ion cloud. Alternatively, the image current detector can be provided with a variety of structures such as double cylinders or triple cylinders.

Figure 4:
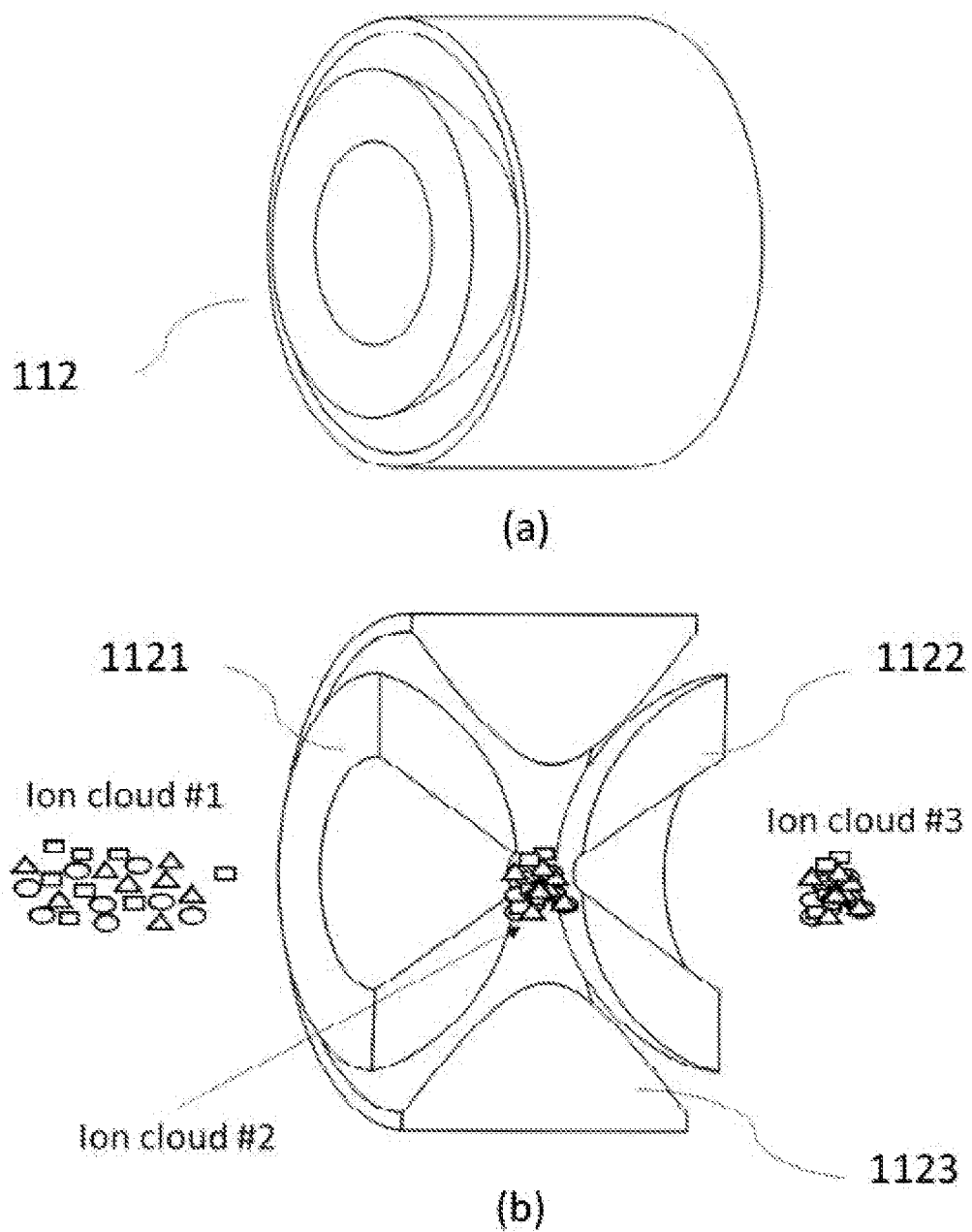
FIG. 4 is a schematic of ion compression device in accordance with some embodiments of the disclosure, panel (a) showing an isometric view, and panel (b) showing a sectional view.

FIG. 4 is a schematic of ion compression device in accordance with some embodiments of the disclosure, panel (a) showing an isometric view, and panel (b) showing a sectional view. In an embodiment as shown in FIG. 4, the ion compression device 112 can be constructed on basis of a 3D ion trap. The ion compression device can comprise three electrodes, including a front endcap 1121, a rear endcap 1122 and a ring electrode 1123 positioned between the front endcap and the rear endcap. The front endcap can be an entrance for the ion clouds and the rear endcap can be the exit. The front endcap and the rear endcap can each be a perforated cone-shaped component with vertexes thereof being spaced from each other. The ring electrode can comprise a convex inner surface. At least a portion of the inner surface of the ring electrode can be interposed between outer surfaces of the front endcap and the rear endcap, such that an inner space is defined by the inner surfaces of the front endcap and the rear endcap and the inner surface of the ring electrode.

Once receiving the start signal from the upstream image current detector, the ion compression device starts to receive from the front endcap and compress the ion cloud within a space defined by the vertex of the front endcap, the vertex of the rear endcap and the convex inner surface of the ring electrode. Once receiving the stop signal from the image current detector, the ion compression device stops receiving ion cloud. At this time, the entire ion cloud, which is generated from a single particle, can be stored in the ion compression device. Due to a collisional cooling effect in 3D ion trap, a duration (e.g., an axial length) of the ion cloud can be narrowed down significantly. Subsequently, the ion compression device can force the compressed ion cloud out of the ion compression device through the rear endcap into the downstream devices.

Though the ion compression device is shown as a 3D ion trap in FIG. 4, the ion compression device can adopt other configuration such as a linear ion trap, an ion funnel, an ion tunnel, an ion carpet, a segmented quadrupole, a segmented multipole and any variants thereof.

Figure 5:
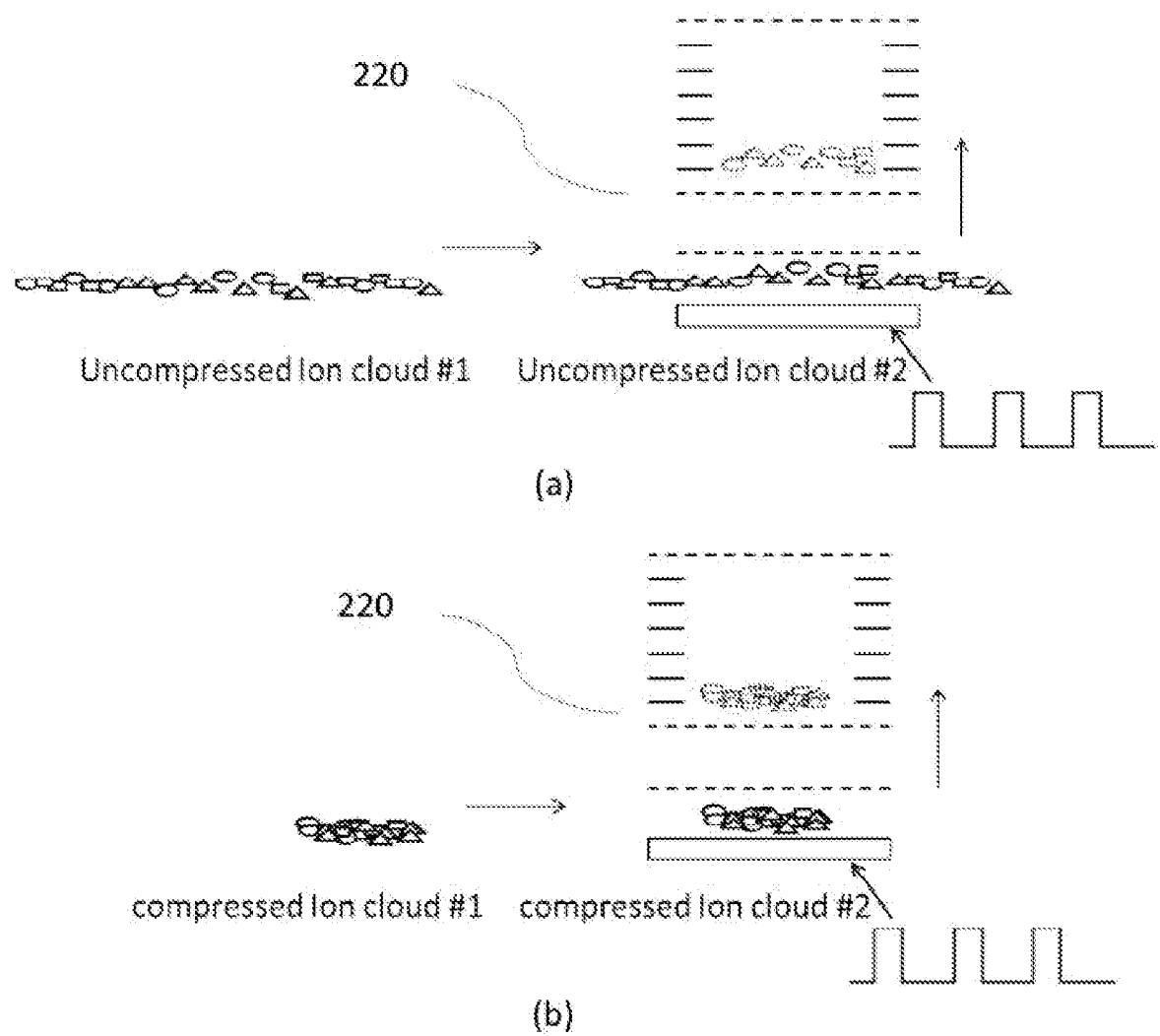
FIG. 5 is a schematic of orthogonal acceleration device in accordance with some embodiments of the disclosure; panel (a) showing an example where the ion cloud is not compressed and only a fraction of the ion cloud can be analyzed, and panel (b) showing the ion cloud is compressed and all the ion cloud can be analyzed.

FIG. 5 is a schematic of orthogonal acceleration device in accordance with some embodiments of the disclosure. Panel (a) of FIG. 5 shows an example where the ion cloud is not compressed and only a fraction of the ion cloud can be analyzed. Panel (b) of FIG. 5 shows an example where the ion cloud is compressed and all the ion cloud can be analyzed. The orthogonal accelerator 220 can apply a pulsed high voltage to generate an acceleration field. The ions in the ion cloud entering the acceleration field can be accelerated by the acceleration field and pushed into the TOF in a pulsed manner. Ions with different masses can obtain same kinetic energy but different velocity. The flight of time in the TOF analyzer for ions having different masses can be different after the ions travelling out a same flight path. Information of mass can be deduced based on a flight of time of ions having different mass.

In the example shown in panel (a) of FIG. 5, when a substantially continuous ion flow, which is continuous at least during a certain time period, flows into the acceleration field of the orthogonal accelerator, only a small fraction of ions can be accelerated and pushed into the TOF, with the rest of ions being lost. For example, only those ions appearing within a width of the acceleration field can be pushed into the TOF and analyzed. This results in a low duty cycle of the TOF mass analyzer. In the example shown in panel (b) of FIG. 5, however, due to a shorter duration of the compressed ion cloud, an entirety of the compressed ion cloud can be accelerated by the orthogonal accelerator. By synchronizing the pulsing of the orthogonal accelerator, an entirety of each ion cloud for each single particle can be accelerated by the orthogonal accelerator and analyzed by the ion detector. Therefore, the duty cycle of the TOF mass analyzer can be greatly improved.

The ions accelerated by the orthogonal accelerator then fly into the field-free region of the TOF analyzer for mass separation. Due to a difference in speed among the ions having different masses, the ions can arrive at the ion detector in a predetermined mass order, for example, from low to high. A corresponding signal sequence can then be generated and further processed by the data processing device to obtain the mass spectrum of the ion cloud, which containing a composition information of the single particle.

Figure 6:
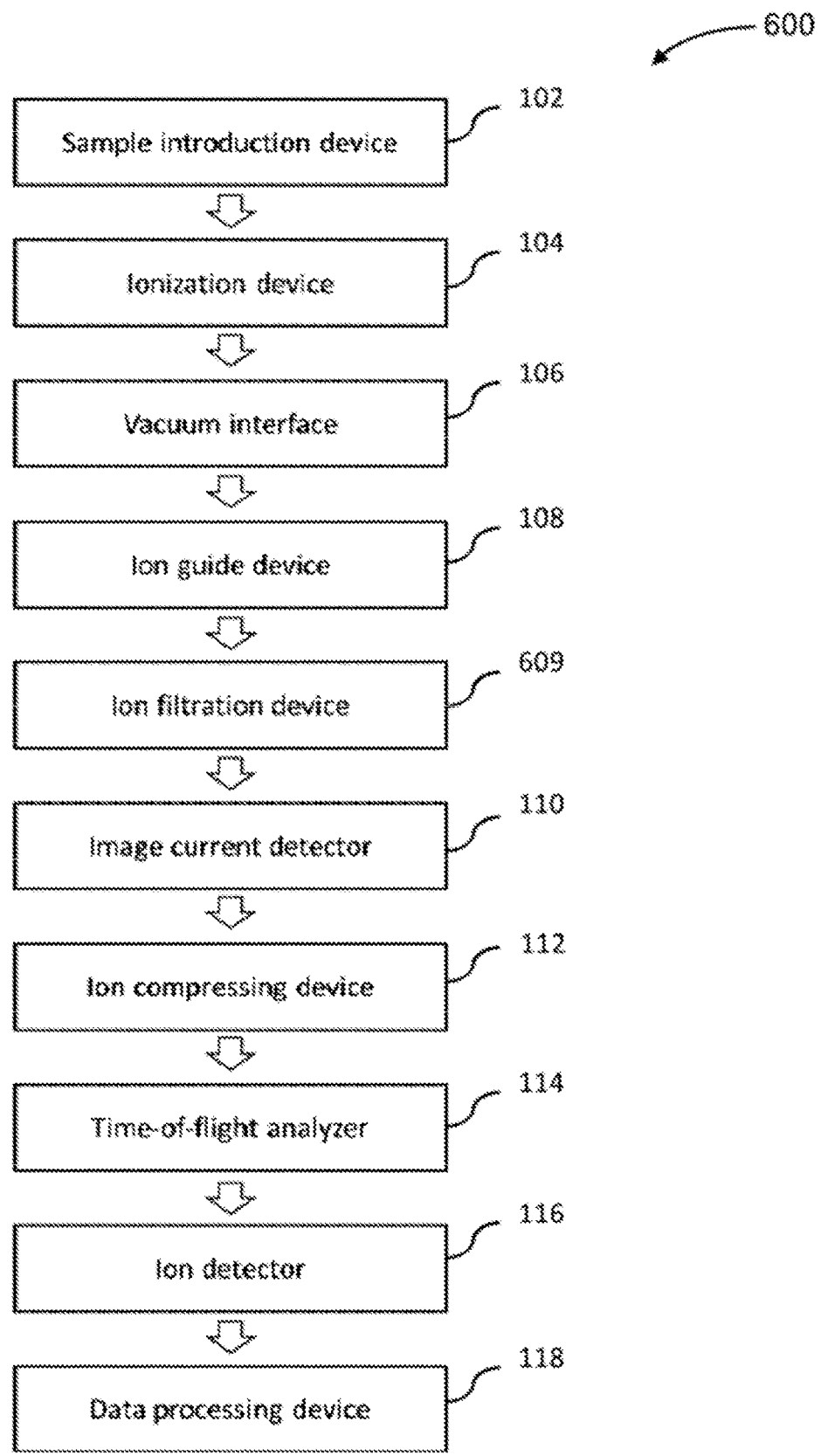
FIG. 6 shows a block diagram of mass spectrometer for analysis of single particles in accordance with alternative embodiments of the disclosure.

FIG. 6 shows a block diagram 600 of mass spectrometer for analysis of single particles in accordance with alternative embodiments of the disclosure. The alternative embodiment of the mass spectrometer shown in FIG. 6, as compared with the embodiment shown in FIG. 1, can comprise an ion filtration device 609. The ion filtration device can be provided at a downstream side of the vacuum interface or the optional ion guide device and at an upstream side of the ion image current detector. The ion filtration device can be configured to remove inference ions from the ion clouds. In an embodiment, the ion filtration device can comprise a quadrupole arrangement or a multipole arrangement.

Figure 7:
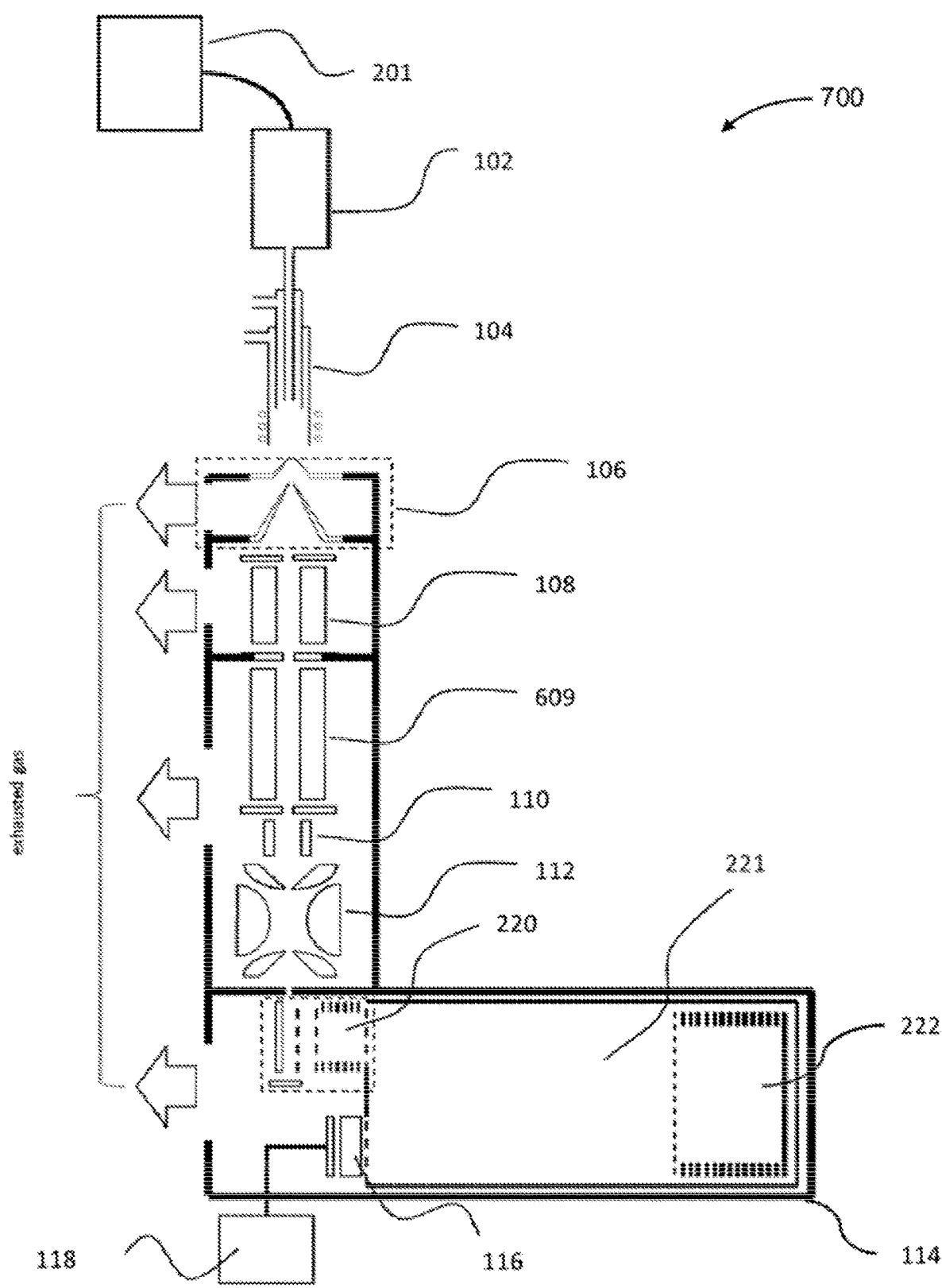
FIG. 7 shows an exemplary structure of a particle mass spectrometry for analysis of single particles in accordance with alternative embodiments of the disclosure.

FIG. 7 shows an exemplary structure of a particle mass spectrometry 700 for analysis of single particles in accordance with alternative embodiments of the disclosure. Samples can be transferred from the sample storage device 201 to the ionization device 104 via the sample introduction device 102. At the ionization device, a separate ion cloud can be generated for each single particle (e.g., a cell). Then, the ion cloud can enter the vacuum system of mass spectrometer through the vacuum interface 104, and be transported to the downstream ion filtration device 609 via the optionally ion guide device 108. The ion filtration device can be used to remove specific inference ions to reduce an interference and a burden of downstream ion device. In an embodiment, the ion filtration device can be provided in the same vacuum chamber where the image current detector and the ion compression device are positioned. Optionally, the ion filtration device can be provided in the same vacuum chamber where the image current detector is positioned. Optionally, the ion filtration device can be provided in a vacuum chamber separate from the vacuum chamber where the image current detector and the ion compression device are positioned. The ion cloud passing through the ion filtration device can fly into the image current detector 110, which determines the start and end time of each ion cloud and generate a start signal and a stop signal for the downstream ion compression device 112 where the ion cloud is axially compressed. An entirety of the compressed ion cloud can be transported into the orthogonal accelerator 220 of the TOF mass analyzer. After the compressed ion cloud is accelerated to a specific kinetic energy by the orthogonal accelerator, it flies into the field-free flight tube 221 for mass separation. Due to a difference in speed among the ions having different masses, the ions can arrive at the ion detector in a predetermined mass order, for example, from low to high. A corresponding signal sequence can then be generated and further processed by the data processing device to obtain the mass spectrum of the ion cloud, which containing a composition information of the single particle.

Figure 8:
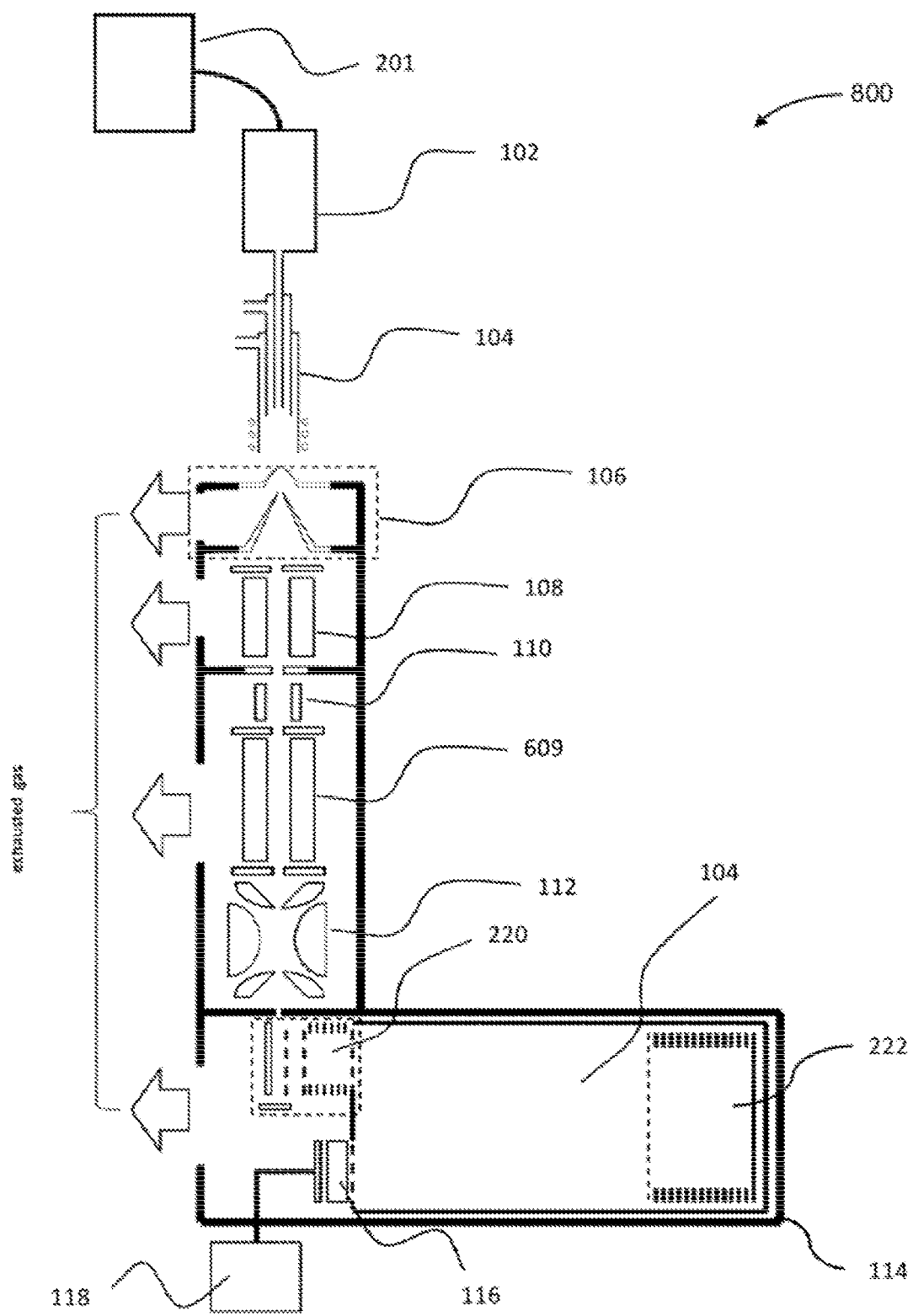
FIG. 8 shows an exemplary structure of a particle mass spectrometry for analysis of single particles in accordance with yet alternative embodiments of the disclosure.

FIG. 8 shows an exemplary structure of a particle mass spectrometry 800 for analysis of single particles in accordance with yet alternative embodiments of the disclosure. In the configuration shown in FIG. 8, as compared with the configuration shown in FIG. 7, the filtration device 609 is positioned between the image current detector 110 and the ion compression device 112. In an embodiment, the ion filtration device can be provided in the same vacuum chamber where the image current detector and the ion compression device are positioned. Optionally, the ion filtration device and the image current detector can be provided in a same vacuum chamber. Optionally, the ion filtration device and the ion compression device can be provided in a same vacuum chamber. Optionally, the image current detector, the ion filtration device, the ion compression device can be provided separate vacuum chambers.

Figure 9:
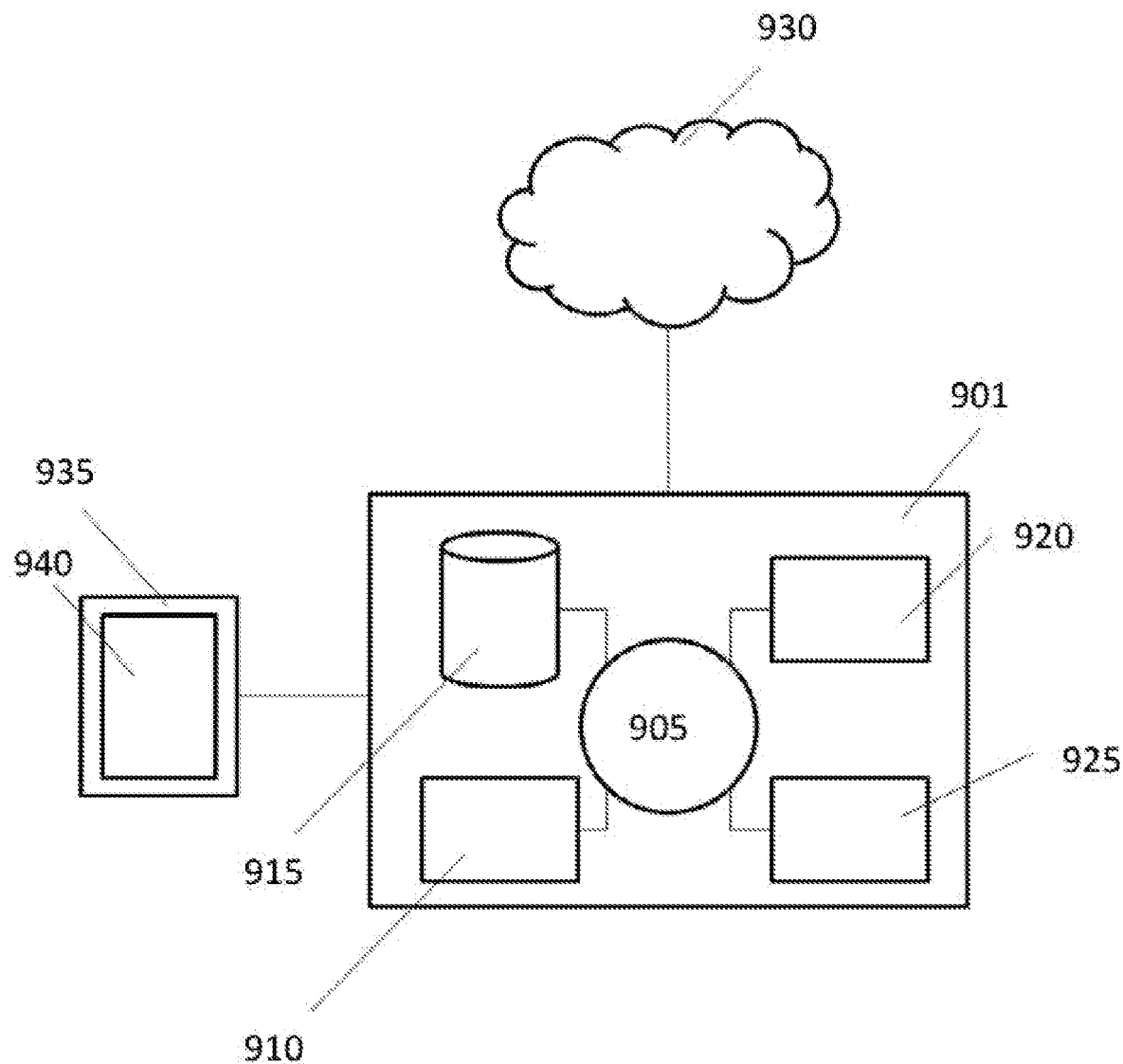
FIG. 9 shows an example of a computer system, provided in accordance with embodiments of the invention.

The present disclosure provides a computer system that is programmed to implement methods and systems of the disclosure. FIG. 9 shows a computer system 901 that is programmed or otherwise configured to implement a signal processing device as described above. The computer system 901 can regulate various aspects of the present disclosure, such as, for example, controlling ion gating components and rendering graphical user interfaces and the other functions as described elsewhere herein. The computer system 901 can be an electronic device of a user or a computer system that is remotely located with respect to the electronic device. The electronic device can optionally be a mobile electronic device.

The computer system 901 includes a central processing unit (CPU, also "processor" and "computer processor" herein) 909, which can be a single core or multi core processor, or a plurality of processors for parallel processing. The computer system 901 also includes memory or memory location 910 (e.g., random-access memory, read-only memory, flash memory), electronic storage unit 915 (e.g., hard disk), communication interface 920 (e.g., network adapter) for communicating with one or more other systems, and peripheral devices 925, such as cache, other memory, data storage and/or electronic display adapters. The memory 910, storage unit 915, interface 920 and peripheral devices 925 are in communication with the CPU 909 through a communication bus (solid lines), such as a motherboard. The storage unit 915 can be a data storage unit (or data repository) for storing data. The computer system 901 can be operatively coupled to a computer network ("network") 930 with the aid of the communication interface 920. The network 930 can be the Internet, an internet and/or extranet, or an intranet and/or extranet that is in communication with the Internet.

The network 930 in some cases is a telecommunication and/or data network. The network 930 can include one or more computer servers, which can enable distributed computing, such as cloud computing. For example, one or more computer servers may enable cloud computing over the network 930 ("the cloud") to perform various aspects of analysis, calculation, and generation of the present disclosure, such as, for example, capturing a configuration of one or more experimental environments; performing usage analyses of products (e.g., applications); and providing outputs of statistics of projects. Such cloud computing may be provided by cloud computing platforms such as, for example, Amazon Web Services (AWS), Microsoft Azure, Google Cloud Platform, and IBM cloud. The network 930, in some cases with the aid of the computer system 901, can implement a peer-to-peer network, which may enable devices coupled to the computer system 901 to behave as a client or a server.

The CPU 909 can execute a sequence of machine-readable instructions, which can be embodied in a program or software. The instructions may be stored in a memory location, such as the memory 910. The instructions can be directed to the CPU 909, which can subsequently program or otherwise configure the CPU 909 to implement methods of the present disclosure. Examples of operations performed by the CPU 909 can include fetch, decode, execute, and writeback.

The CPU 909 can be part of a circuit, such as an integrated circuit. One or more other components of the system 901 can be included in the circuit. In some cases, the circuit is an application specific integrated circuit (ASIC).

The storage unit 915 can store files, such as drivers, libraries and saved programs. The storage unit 915 can store user data, e.g., user preferences and user programs. The computer system 901 in some cases can include one or more additional data storage units that are external to the computer system 901, such as located on a remote server that is in communication with the computer system 901 through an intranet or the Internet.

The computer system 901 can communicate with one or more remote computer systems through the network 930. For instance, the computer system 901 can communicate with a remote computer system of a user (e.g., a user of an experimental environment). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 901 via the network 930.

Methods as described herein can be implemented by way of machine (e.g., computer processor) executable code stored on an electronic storage location of the computer system 901, such as, for example, on the memory 910 or electronic storage unit 915. The machine executable or machine readable code can be provided in the form of software. During use, the code can be executed by the processor 909. In some cases, the code can be retrieved from the storage unit 915 and stored on the memory 910 for ready access by the processor 909. In some situations, the electronic storage unit 915 can be precluded, and machine-executable instructions are stored on memory 910.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 901 can include or be in communication with an electronic display 1235 that comprises a user interface (UI) 940 for providing, for example, the various components (e.g., lab, launch pad, control center, knowledge center, etc) of the model management system. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 909. The algorithm can, for example, generate instructions to operate one or more component of a sample transport system.

It should be understood from the foregoing that, while particular implementations have been illustrated and described, various modifications can be made thereto and are contemplated herein. It is also not intended that the invention be limited by the specific examples provided within the specification. While the invention has been described with reference to the disclosure, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A mass spectrometer for analysis of single particles, said mass spectrometer comprising:
    a sample introduction device configured to sequentially generate and transfer the single particles;
    an ionization device configured to generate an individual ion cloud from each of the single particles received from the sample introduction device;
    a vacuum interface configured to transport the ion clouds from the ionization device with aid of a vacuum;
    an ion image current detector configured to receive the ion clouds from the vacuum interface and collecting timing information of each of the ion clouds passing through the ion image current detector;
    an ion compression device configured to (1) receive an individual ion cloud from the ion image current detector, (2) axially compress the received ion cloud based on the timing information of the individual ion cloud, and (3) transport the compressed ion cloud;
    a time-of flight (TOF) mass analyzer configured to receive the compressed ion clouds from the ion compression device and separate ions having different masses within the compressed ion clouds to arrive at an ion detector at different times; and
    a data processing device configured to process an ion flow signal generated from the ion detector and form a mass spectrum for identification of the ion clouds.

2. The mass spectrometer of claim 1, wherein the single particles are tagged with metal isotopes.

3. The mass spectrometer of claim 2, wherein the ion clouds comprise ion clouds of the metal isotopes.

4. The mass spectrometer of claim 1, wherein the single particles are single cells or polymer microspheres.

5. The mass spectrometer of claim 1, wherein the sample introduction device is configured to sequentially receive and transfer the single particles from a sample storage device.

6. The mass spectrometer of claim 1, wherein the ionization device is an inductively coupled plasma (ICP) ionization device.

7. The mass spectrometer of claim 6, wherein the ionization device is configured to evaporate, atomize, and ionize the single particles.

8. The mass spectrometer of claim 6, wherein the ionization device is configured to generate monoatomic or polyatomic ions from the single particles.

9. The mass spectrometer of claim 1, wherein the vacuum interface comprises two or more adjacent vacuum chambers.

10. The mass spectrometer of claim 1, further comprising an ion guide device positioned at a downstream side of the vacuum interface and at an upstream side of the ion image current detector, wherein the ion guide device is configured to receive the ion clouds from the vacuum interface and transport the ion clouds.

11. The mass spectrometer of claim 10, wherein the ion guide device utilizes a quadrupole arrangement, a multipole arrangement, an electrostatic lens, an ion tunnel or an ion funnel.

12. The mass spectrometer of claim 1, wherein the ion compression device is selected from a group comprising a three-dimensional (3D) ion trap, a linear ion trap, an ion funnel, an ion tunnel, an ion carpet, a segmented quadrupole and a segmented multipole.

13. A method for analyzing single particles via a mass spectrometer, said method comprising:
    (a) sequentially generating and transferring the single particles at a sample introduction device;

(b) generating, with aid of an ionization device, ion clouds from the single particles received from the sample introduction device;

(c) transporting, using a vacuum interface, the ion clouds from the ionization device with aid of a vacuum;

(d) receiving, via an ion image current detector, the ion clouds from the vacuum interface, and collecting timing information of the ion clouds passing through the ion image current detector;

(e) receiving, at an ion compression device, an individual ion cloud from the ion image current detector, axially compressing the received ion cloud based on the timing information of the individual ion cloud, and transporting the compressed ion clouds;

(f) receiving, at a time-of flight (TOF) mass analyzer, the compressed ion clouds and separating ions having different masses within the compressed ion clouds to arrive at an ion detector at different times; and (g) processing, via a data processing device, an ion flow signal from the ion detector and form a mass spectrum for identification of the ion clouds.

14. The method of claim 13, wherein the single particles are tagged with metal isotopes.

15. The method of claim 13, wherein the single particles are single cells.

16. The method of claim 13, wherein the single particles are polymer microspheres.

17. The method of claim 13, wherein the ionization device is selected from the group comprising inductively coupled plasma ionization device, secondary ion mass spectrometry ionization device, electrospray ionization device, atmospheric pressure chemical ionization device, and atmospheric pressure photoionization device.

18. The method of claim 13, wherein the vacuum interface comprises two or more adjacent vacuum chambers.

19. The method of claim 13, further comprising, subsequent to (c) and prior to (d), (h) receiving, via an ion guide device, the ion clouds from the vacuum interface, and transporting the ion clouds.

20. The method of claim 19, further comprises, subsequent to (h) and prior to (d), (i) effecting an ion filtration, via an ion filtration device, the ion clouds from the ion guide device, and transporting the filtered ion clouds.

* * * * *